US006083154A

United States Patent [19]
Liu et al.

[11] Patent Number: 6,083,154
[45] Date of Patent: Jul. 4, 2000

[54] SURGICAL INSTRUMENTATION AND METHOD FOR RETRACTING AND SHIFTING TISSUES

[75] Inventors: Mingyah Liu, Bourg la Reine; Jean-Paul Steib, Strasbourg; Jean-Francois d'Amore, Montevrain; Philippe Bouquet, Lamorlaye, all of France

[73] Assignee: Sofamor S.N.C., Roissy CDG Cedex, France

[21] Appl. No.: 09/177,245

[22] Filed: Oct. 22, 1998

[30] Foreign Application Priority Data

Oct. 23, 1997 [FR] France ................................. 97 13309

[51] Int. Cl.⁷ ................................................. A61B 17/02
[52] U.S. Cl. ........................................... 600/234; 600/231
[58] Field of Search ..................... 600/201, 205, 600/210, 231, 232, 233, 234, 235, 219

[56] References Cited

U.S. PATENT DOCUMENTS

| | | |
|---|---|---|
| 2,438,646 | 3/1948 | Pulliam .................................... 600/231 |
| 2,473,266 | 6/1949 | Wexler ................................. 600/234 X |
| 2,623,517 | 12/1952 | Barlow et al. ....................... 600/234 X |
| 3,509,873 | 5/1970 | Karlin et al. ......................... 600/231 X |
| 3,572,326 | 3/1971 | Jensen . |
| 3,964,480 | 6/1976 | Froning .................................... 128/215 |
| 4,817,587 | 4/1989 | Janese . |
| 5,125,396 | 6/1992 | Ray . |
| 5,167,223 | 12/1992 | Koros et al. . |
| 5,363,841 | 11/1994 | Coker . |
| 5,728,046 | 3/1998 | Mayer et al. ............................. 600/210 |
| 5,795,291 | 8/1998 | Koros et al. ............................. 600/232 |
| 5,928,139 | 7/1999 | Koros et al. ............................. 600/205 |
| 5,931,777 | 8/1999 | Sava ..................................... 600/235 X |
| 5,944,658 | 8/1999 | Koros et al. ............................. 600/232 |

FOREIGN PATENT DOCUMENTS

| | | |
|---|---|---|
| 0 077 159 A1 | 10/1982 | European Pat. Off. . |
| 0 632 997 A1 | 7/1994 | European Pat. Off. . |
| 0 749 724 A1 | 3/1996 | European Pat. Off. . |
| 2 692 468 | 6/1992 | France . |
| WO 95/35180 | 6/1995 | WIPO . |

OTHER PUBLICATIONS

AESCUPLAP Brochure; pp. 68–83; Dr. Wolfhard Caspar, Department of Neurosurgery; University of Saarland (no date).

Primary Examiner—Jeffrey A. Smith
Attorney, Agent, or Firm—Woodard, Emhardt, Naughton, Moriarty & McNett

[57] ABSTRACT

This instrumentation comprises valves (2) for shifting aside tissues and vessels, pins for fixing each valve (2) to the spine, each valve (2) comprising for this purpose sleeves (6) in which the pin (5) is slidable; the instrumentation further comprises, for each valve (2), an articulated device (7) comprising a clamp (12) for clamping a rod (13) fixed to the valve (2); the clamp (12) may be articulated to a ball and oriented in all directions in space while the rod (13) and the valve (2) are adjustable in translation in the clamp (12); the articulated devices (7) are adjustably slidably mounted on a support frame (8). The instrumentation further comprises a push member which is capable of bearing against the valves (2) and preventing them from slipping on the surface of the spine while they are being placed in position. This device permits conveniently orienting the valves (2) in all directions and in translation.

39 Claims, 6 Drawing Sheets

SURGICAL INSTRUMENTATION AND METHOD FOR RETRACTING AND SHIFTING TISSUES

BACKGROUND

The present invention relates to surgical instrumentation, and more particularly, but not exclusively relates to instrumentation for retracting and shifting aside soft tissues and vessels for the purpose of approaching the spine from the front to provide an operating area for spinal surgery.

Heretofore, the method employed by surgeons for this purpose consisted in employing "valves," usually three in number, formed by plates having bent lower end portions. These valves are manually inserted by shifting aside the blood vessels, the nerves and the soft tissues by means of their bent end portions which come to bear against the bone surface of the spine.

The valves may be completed by pins which have ends inserted in the spine. The valves can be slid along these pins. Another technique teaches connecting the valves to the edge of the operating table so as to maintain them in the desired position and clear the operating area.

This device is however relatively rudimentary and not fully convenient to use, in particular for maintaining the valves in the desired precise angular orientation. The correct fixing of the valves on the spine is important in that it avoids the risk of the vessels entering the operating area.

Thus, there is a need for improved surgical instrumentation. The present invention meets this need and has other benefits and advantages.

SUMMARY OF THE INVENTION

One form of the present invention includes surgical instrumentation to retract tissue to maintain an operating area.

In another form, surgical instrumentation to perform a surgical intervention on a patient's spine includes a frame, a number of valves, and a number of articulated devices each adapted to be rigidly fixed to the frame. The articulated devices are each used to mount a respective one of the valves in a selected orientation to shift aside tissues so that an operating field may be maintained.

In yet another form, surgical instrumentation of the present invention includes a frame, a number of valves, and a number of articulated devices each corresponding to one of the valves and each being adapted to be rigidly fixed to the frame in a spaced-apart relationship from one to another. The devices each include a first portion coupled to a respective one of the valves and a second portion contacting the first portion in a bearing relationship. The devices are each selectively operable to permit the first portion to slidably pivot about the second portion with two degrees of freedom to adjust angular position of the respective one of the valves over a range of angles. The devices are also each operable to selectively clamp the respective one of the valves, the first portion, and the second portion together; with the respective one of the valves being in an angular position selected from the range to retract tissue in contact therewith to establish an operating area along a patient's spine.

In a further form, surgical instrumentation of the present invention includes a retractor and an articulated device operable to connect to the retractor. The device includes a ball joint to angularly position the retractor over a range of angles when the retractor is coupled thereto. The device is arranged to selectively fix the retractor at an angle selected from this range. Additional retractors and devices may be utilized and interconnected by a frame in a spaced-apart relationship.

An additional form of the present invention includes a retractor and an articulated device including a retractor mount and a pin. The mount defines a passage through which the pin passes. This passage is shaped to selectively move the mount relative to the pin with two degrees of freedom over a range of different angular positions and correspondingly position the pin over a range of different locations within the passage. The retractor is angularly adjustable with the mount when mounted to the first device. The device is operable to clamp the mount and pin together to rigidly fix the retractor at a desired angle selected from the range of angles when the retractor is mounted to the device. Additional retractors may be clamped by additional articulated devices and interconnected by a frame in a spaced-apart relationship to maintain an operating field.

In still another form of the present invention, surgical instrumentation includes a retractor and an articulated device including a mount coupled to the retractor and a bearing member. The bearing member includes a rounded shoulder and a stem projecting from the shoulder. The mount defines a passage receiving the shoulder in contact with the mount. This passage is shaped to permit movement of the mount along the shoulder while in contact therewith to angularly adjust the retractor. The stem extends through the passage to limit angular adjustment of the retractor to a first range. The articulated device is operable to selectively clamp the rod, the mount, and the bearing member together to fix the retractor at an angle selected from the range. Further retractors and corresponding articulated devices may be utilized and interconnected by a frame to maintain a desired operating area.

Another form of the present invention is a technique for performing surgery on a patient's spine that includes mounting a first valve on a frame with a first articulated device. The first valve is fixed to a first rod and the first device includes a mount defining a cavity for receiving the first rod and a bearing member engaged with the mount. This technique also includes sliding the first rod in the cavity to provide a desired translational position of the first rod relative to the first device and pivoting the mount about the bearing member to select a desired angular position of the first rod from a range of angles generally corresponding to a cone. The first rod is clamped in the desired translational and angular position. A second valve fixed to a second rod is connected on the frame with a second articulated device. The first valve and the second valve are oriented to shift aside tissue to maintain an operating field along the patient's spine.

A further form of the present invention is a surgical technique of mounting each of a number of valves to a corresponding one of a number of articulated devices connected to a frame. Also, each of the valves is fixed to a patient's spine with a respective one of a number of fixation pins. This pin may include a thread to engage bone. Each of the valves is clamped in a desired translational and rotational position with the corresponding one of the articulated devices.

In another aspect, the present invention comprises at least two retractors each having a valve whereby it is possible to adjust and more easily maintain the desired precise angular orientation of each valve and its contract with the spine. This surgical instrumentation may comprise means for fixing each valve to the spine, a frame adapted to interconnect the valves, and an articulated device associated with each valve, connected to the frame and permitting positioning and orienting the corresponding valve in translation and in rotation. The fixing means may comprise, for each valve, a sleeve in which there is slidable a smooth or screw-threaded pin for fixing to the spine.

According to another advantageous embodiment, the fixing means comprise in each valve an axial longitudinal passage in which is slidable a fixation pin. Preferably, this fixation pin has a screw-threaded end portion and an opposite end portion shaped for receiving a screwing tool and bearing against the valve so as to exert on the latter a force for maintaining it in position on the spine.

According to another feature of the invention, each articulated device comprises a clamp for clamping a rod having an end fixed to the valve, this rod being adjustable in translation in the clamp, and the latter being articulated to a ball slidably mounted on a pin fixed to a fork which is supported by the frame and adjustable in position in the latter. Thus the clamp, and consequently the rod fixed to the valve, may be oriented in all directions on its articulation ball, the position of the valve in translation being moreover adjustable by moving its support rod in translation in the clamp. The clamp may also be integrally connected or fixed directly to the valve, or to a handle fixed to the valve, the connecting rod between the valve and the handle being eliminated, if desired.

To use this instrumentation, one surgical method comprises placing the valves and their articulated devices on the support frame in the desired position in translation and in rotation, while shifting aside soft tissues and vessels, mounting on each valve the pin for fixing to the spine in the required position for holding the soft tissues and the vessels away from the operating area, and exerting on the valve a force causing it to bear against the surface of the spine.

Further objects, features, forms, benefits, aspects, and advantages of the invention will appear from the following description, with reference to the accompanying drawings, which illustrate several embodiments of the invention by way of a non-limitative example.

DESCRIPTION OF PREFERRED EMBODIMENTS

Figure 1:
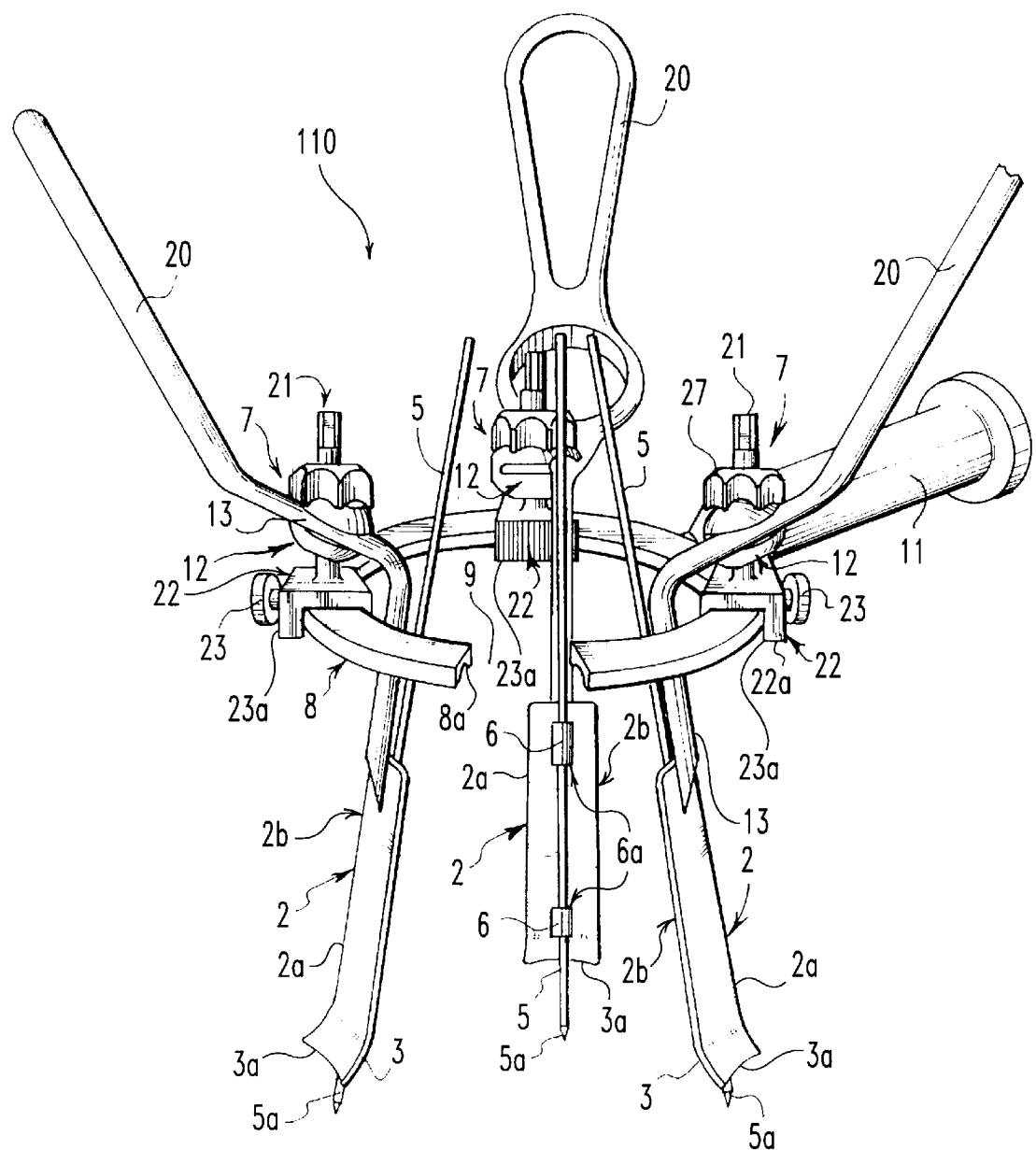
FIG. 1 is a perspective view to a small scale of surgical instrumentation of one embodiment of the present invention for retracting and shifting aside soft tissues and vessels according to the invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The surgical instrumentation 110 illustrated in the drawings is adapted to enable a surgeon to effect a retraction and a shifting aside of soft tissues, vessels and nerves so as to clear an operating area on the spine from the front, which permits effecting a subsequent surgical intervention, for example for installing spinal prostheses.

Figure 5:
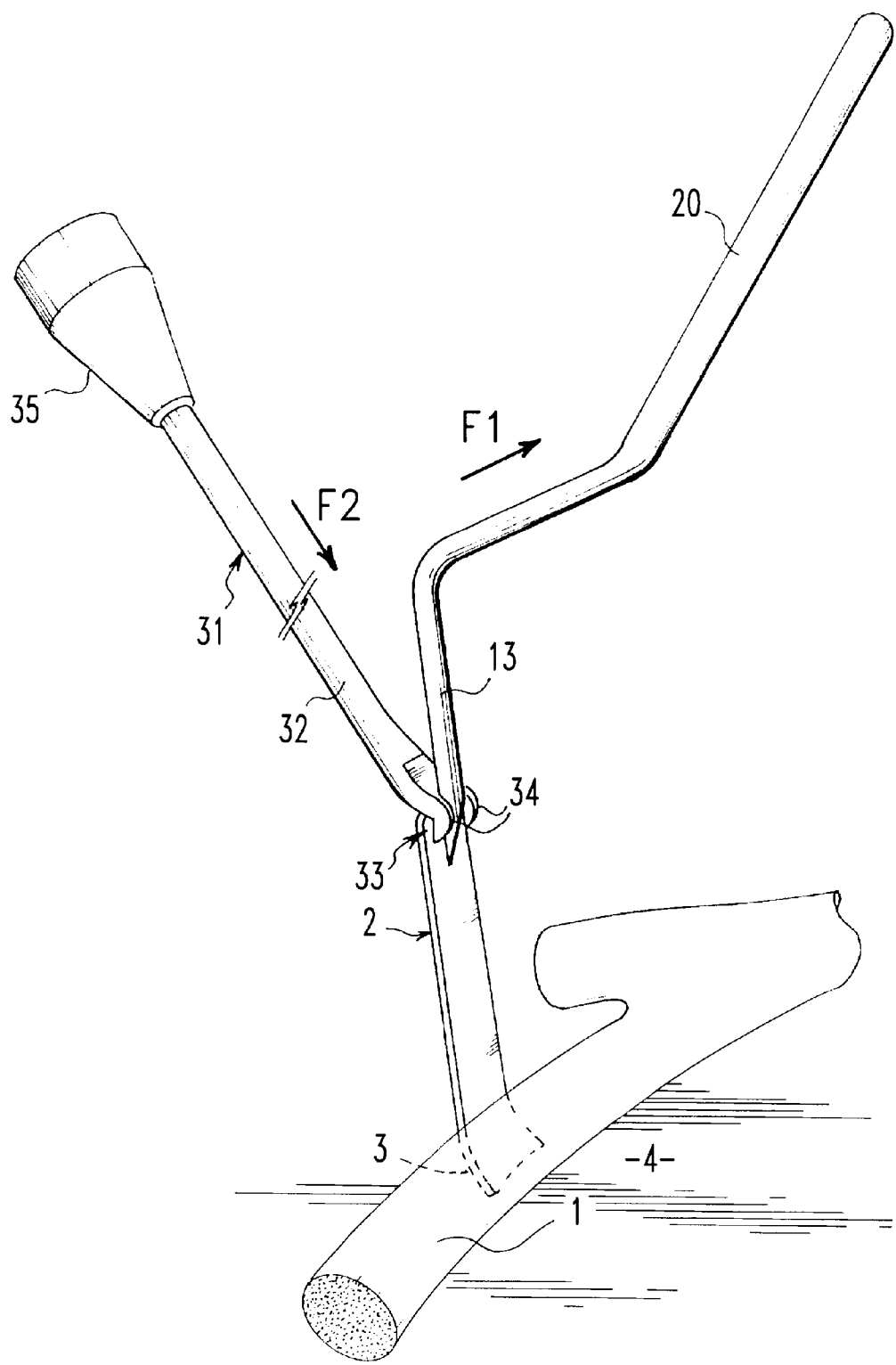
FIG. 5 is a perspective view illustrating the operation of the push member of FIG. 4 with one of the valves of the instrumentation of FIG. 1.

Referring to FIGS. 1 and 5, instrumentation 110 comprises (FIG. 1) at least two retractors 2b each having a valve 2 for shifting aside soft tissues and blood vessels such as 1 (FIG. 5), namely three valves 2 in the illustrated embodiment, formed by elongate plates 2a whose lower end portion 3 is bent for more conveniently retaining the vessels 1, and bearing against the bone surface 4 of the spine. Each lower portion 3 terminates in a slightly curved edge 3a.

Each of the three valves 2 is provided with means for fixing it to the bone 4 of the spine. In the embodiment shown in FIG. 1, these means comprise a smooth fixation pin 5 having a pointed end 5a which is slidable in sleeves or bushings 6 fixed to the corresponding valves 2. The sleeves 6 may be, for example, two in number for each valve 2 and made in one piece with the latter on the side thereof opposite to their bent end portion 3. Ech sleeve 6 defines a fixation pin retaining passageway 6a. As a variant, the pins 5 may also be screw threaded.

Instrumentation 110 further comprises, for each retractor 2b, an articulated device 7 whereby it is possible to orient the valve 2 in all directions in space, and a frame 8 adapted to interconnect and support the articulated devices 7 and valves 2. In the illustrated embodiment, the frame 8 comprises a generally circular ring in one piece interrupted by a cutaway part 9 on an angular sector suitable for conveniently placing in position the articulated devices 7 and shifting valves 2 into position. The generally circular frame 8 may be advantageously provided with a handle 11 to enable the surgeon to handle the frame 8.

Figure 2:
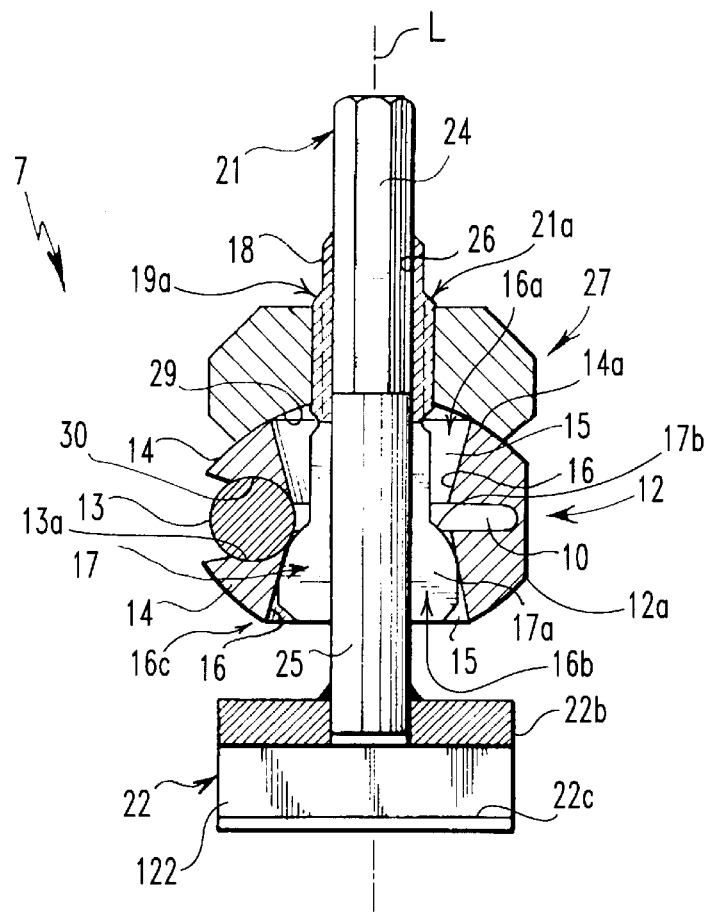
FIG. 2 is a partial, sectional view to a larger scale relative to FIG. 1, of an articulated device associated with each valve.
Figure 3:
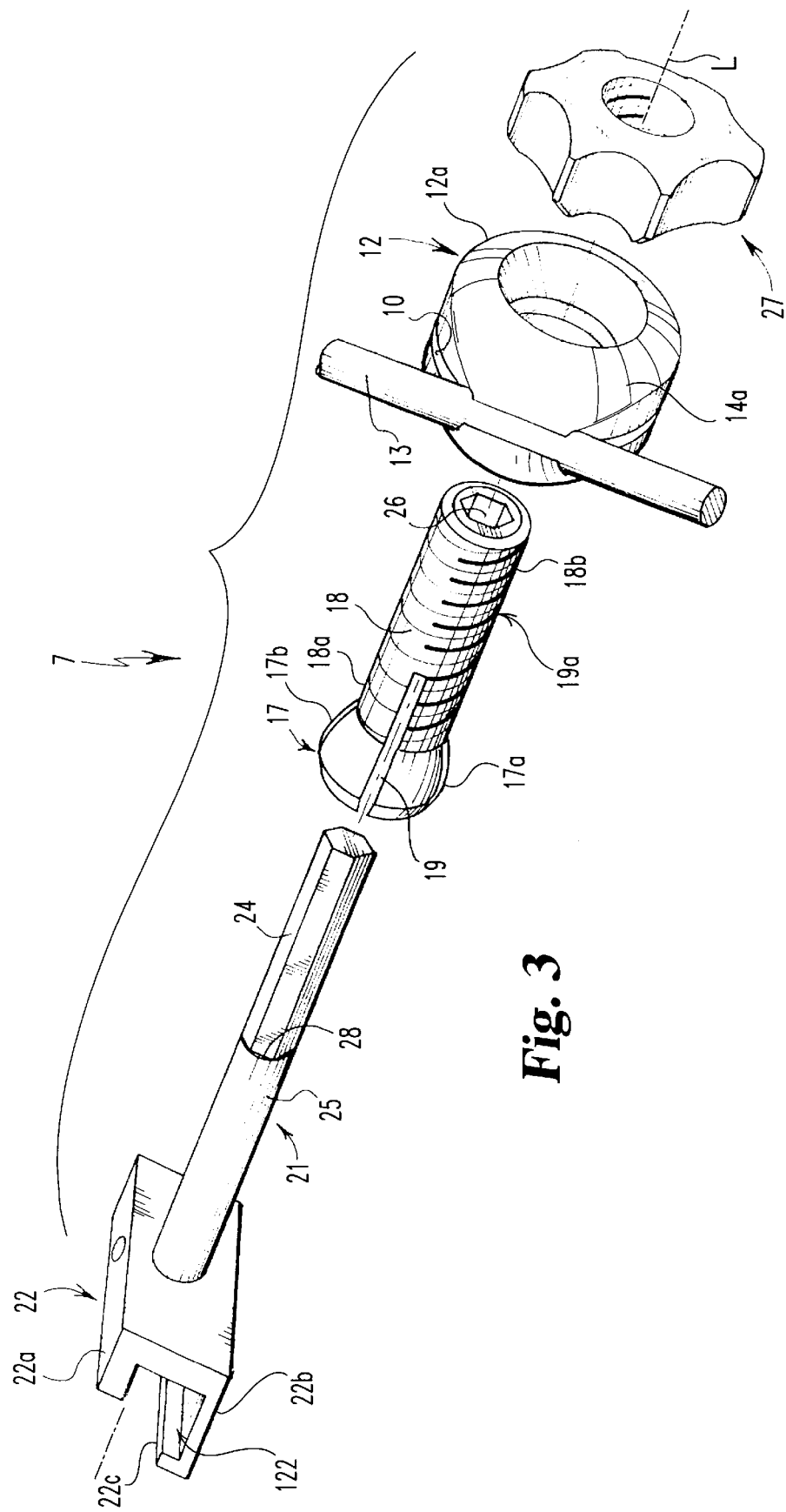
FIG. 3 is an exploded perspective view of the articulated device of FIG. 2.

Referring additionally to FIGS. 2 and 3, each articulated device 7 comprises a clamp 12 for clamping a shifting rod 13 of each retractor 2b. Each shifting rod 13 has an end coupled or fixed to a corresponding valve 2. The shifting rod 13 extends throughout a cavity 13a formed by two complementary semi-cylindrical recesses 30 provided in two respective branches or jaws 14 of the clamp 12, transversely of a slot 10 separating the jaws 14. The rod 13 is thus adjustable together with the valve in translation in its cavity 13a.

Clamp 12 serves as a retractor mount 12a for device 7. In the depicted embodiment, mount 12a includes cavity 13a for receiving shifting rod 13 of retractor 2b for positioning relative to other portions of device 7. Provided in each jaw 14 is a respective axial opening 15 whose inner surface defines a conical bearing surface 16. Opening 15 through each jaw 14 and slot 10 intersect to define passage 16a through mount 12a. Passage 16a may intersect cavity 13a via slot 10 as depicted in FIG. 2.

The device 7 further comprises a hollow spherical ball-shaped part or ball 17 on which one of the bearing surfaces 16 may bear and which is connected to and extended by a screw-threaded sleeve 18. Sleeve 18 has base portion 18a connected to ball 17 opposite top portion 18b. Preferably, ball-shaped part 17 and sleeve 18 are integrally connected. A suitable number of slots 19 are provided in the wall 17a of the ball 17 and in the base portion 18a of the sleeve 18 (FIG. 3) to impart a certain flexibility to the wall 17a of ball 17.

Collectively, ball-shaped part 17 and sleeve 18 comprise bearing member 19a. Passage 16a is shaped to define a generally conically shaped socket 16b to receive ball-shaped part 17 of bearing member 19a, and to permit sleeve 18 to extend through mount 12a. Conical bearing surface 16 about socket 16b contacts rounded shoulder 17b of ball part 17 so that mount 12a may slidably ride thereon before components of device 7 are rigidly clamped together. Collectively, socket 16b and ball part 17 of bearing member 19a constitute ball joint 16c to pivotally adjust mount 12a about bearing member 19a with two degrees of freedom.

The ball part 17 and sleeve 18 are slidably mounted on device pin 21. Collectively, sleeve 18 and pin 21 provide a stem 21a extending out of passage 16a of mount 12a. One end of pin 21 is fixed to fork 22, which is U-shaped so as to be capable of capping the corresponding section of the frame 8 and of being adjustable in position on the frame 8. This adjustment may be effected for example by means of a knurled knob 23 having a threaded stem, which engages a tapped hole through the outer branch 22a of the fork 22. Inner branch 22b of fork 22 is opposite inner branch 22a. Inner branch 22b includes lip 22c. Branches 22a and 22b define channel 122 shaped and sized to receive frame 8. Lip 22c engages an inner underside portion 8a of frame 8, and may be utilized to provisionally retain fork 22 on frame 8 while knob 23 is being adjusted. Collectively, fork 22 and knob 23 provide frame fastener 23a for selectively and rigidly fastening device 7 to frame 8. Once each device 7 is fixed to frame 8, frame 8 effectively interconnects devices 7, and correspondingly retractors 2b with respective valves 2, in a selected spaced apart relationship.

The upper part 24 of the pin 21 has a polygonal section, for example a hexagonal section, while the part 25 thereof connected to the fork 22 is cylindrical. The polygonal section 24 is adapted to be fitted in a complementary female section 26 of the sleeve 18, which enables the latter and the ball 17 to be locked against rotation relative to the pin 21. Generally, the part 24 of the pin 21 engaged in the sleeve 18 may have a non-circular section and is fitted in a matching female section of the sleeve 18 so as to lock the latter and the ball 17 against rotation about the pin 21.

The end of the part 25 of the pin 21 situated at the junction with its sectional part 24 forms a transverse shoulder 28 for stopping the sleeve 18 and the ball 17 when these two members, which are in one piece, are mounted on the pin 21 on which they are retained in the position illustrated in FIG. 2. The clamp 12, optionally provided with the rod 13, may be placed in position coaxially with the sleeve 18 through one or the other of its openings 15, until it bears against the ball part 17 with one of its conical bearing surfaces 16. The taper of the openings 15 associated with the generally spherical shape of the ball 17 permits orienting the clamp 12 and mount 12a, and therefore the rod 13 and the valve 2, in all directions within a cone.

For the embodiment depicted in FIG. 2, conical bearing surfaces 16 are generally flat, each being oriented to define an angle of about 15 degrees relative to axis L along the length of pin 21 and device 7. Correspondingly, the angular adjustment range of device 7 as depicted is approximately ±15 degrees relative to axis L about two mutually perpendicular pivot axes that are also each perpendicular to axis L. Said differently, angular position of device 7 as depicted may be selected from a range of angles corresponding to a cone subtending an angle of about 30 degrees. The conical angular selection geometry provided by ball joint 16c corresponds to two degrees of freedom of rotational movement each about a different one of the mutually perpendicular pivot axes. Notably, stem 21a limits the angular range by encountering a side of passage 16a and bearing against a corresponding conical bearing surface 16 in the upper portion of mount 12a opposite lower conical bearing surface 16 defining socket 16b. In other embodiments, a different angular range or selection geometry may be utilized as would occur to those skilled in the art.

The length of the pin 21 is such that its sectional part 24 axially extends beyond the sleeve 18 on which the locking nut 27 is screwed until the latter is applied against upper bearing surface 14a of upper jaw 14 of the clamp 12. Advantageously, surface 14a of the upper jaw 14 is spherical or ball-shaped and cooperates with a corresponding concave, spherically-shaped bearing surface 29 on the locking nut 27.

Consequently, each articulated device 7 permits a combination of the following adjustments: a first adjustment in height of the ball 17 and therefore of the clamp 12 and rod 13 on the pin 21, a second adjustment in angular orientation in the three directions in space of the clamp 12 on the ball 17, once the height of the latter has been adjusted on the pin 21; an adjustment of the position in translation of the rod 13 in the clamp 12 and therefore of valve 2. When these various adjustments have been made, nut 27 is threaded on sleeve 18 of stem 21a and tightened to bear against mount 12a, which clamps rod 13 received in cavity 13a, mount 12a, and bearing member 19a together to fix retractor 2b in a selected translational and angular position selected from a range generally corresponding to a cone. The nut 27 permits locking all of the components in position, the flexibility of the ball 17 enabling it to clamp on the part 25 of the pin 21.

Each rod 13 may be advantageously extended by a handling handle 20, only one of which is depicted in FIG. 1. Handle 20 may be eliminated in other embodiments, with clamp 12 (or mount 12a) being directly fixed either to retractor 2b or valve 2, to handle 20, or arranged in such other manner as would occur to those skilled in the art.

Figure 4:
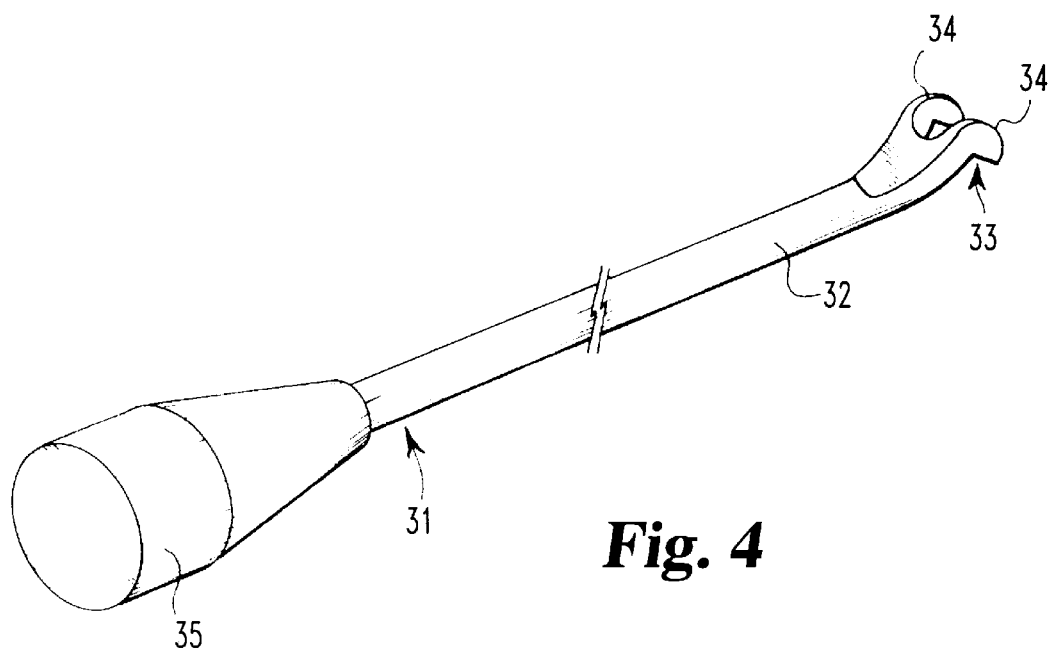
FIG. 4 is a perspective view of a push member which may be combined with the instrumentation of FIGS. 1–3 for exerting on a valve a force with which it bears against the spine.

The instrumentation is advantageously completed by a push member 31 shown in FIGS. 4 and 5. Push member 31 is formed by a rod provided at one of its ends 32 with a nose 33 for hooking on the upper end of a valve 2. As illustrated in FIG. 4, the nose 33 may have two curved branches 34 separated by a gap slightly larger than the diameter of a rod 13 so as to be capable of fitting around the latter on the upper end of a valve 2 (FIG. 5). The push member 31 is preferably provided with a handling handle 35 at the end remote from the nose 33.

Thus, while the surgeon exerts a principally pulling force F1 on a valve 2 whose bent end portion 3 moves away a vessel 1 or soft tissues (FIG. 5), he can exert a force F2 with his other hand, or with the aid of an assistant, by means of the push member 31 whose nose 33 is engaged on the valve 2 for causing the valve 2 to bear against the bone surface 4 in the chosen position. In this way, risk of a slipping of the valve 2 is reduced during the operation for shifting aside the tissues and the vessels.

To use the instrumentation just described, the surgeon proceeds substantially in the following manner:

The surgeon places the articulated devices 7, rods 13 and the associated valves 2 in a suitable number, i.e., two, three or more valves, in position on the annular frame 8. The valves are each adjusted in the desired angular orientation by means of the articulated devices 17 and fixed to the bone 4 of the spine by a corresponding pin 5 in the desired position. The valves 2 are then fixed to the frame 8 by tightening nuts 27 to bear against corresponding clamps 12 (or mounts 12a). The positioning of the valves 2 may be facilitated by the use of push member 31 for each valve 2 in succession, as previously described.

According to another possible surgical method for using the instrumentation, at least one valve 2 is first of all fixed in position on the spine 4, then the frame 8 is fixed with the valve(s), then the other valves 2 are adjusted in position and then fixed one by one to the frame.

Figure 6:
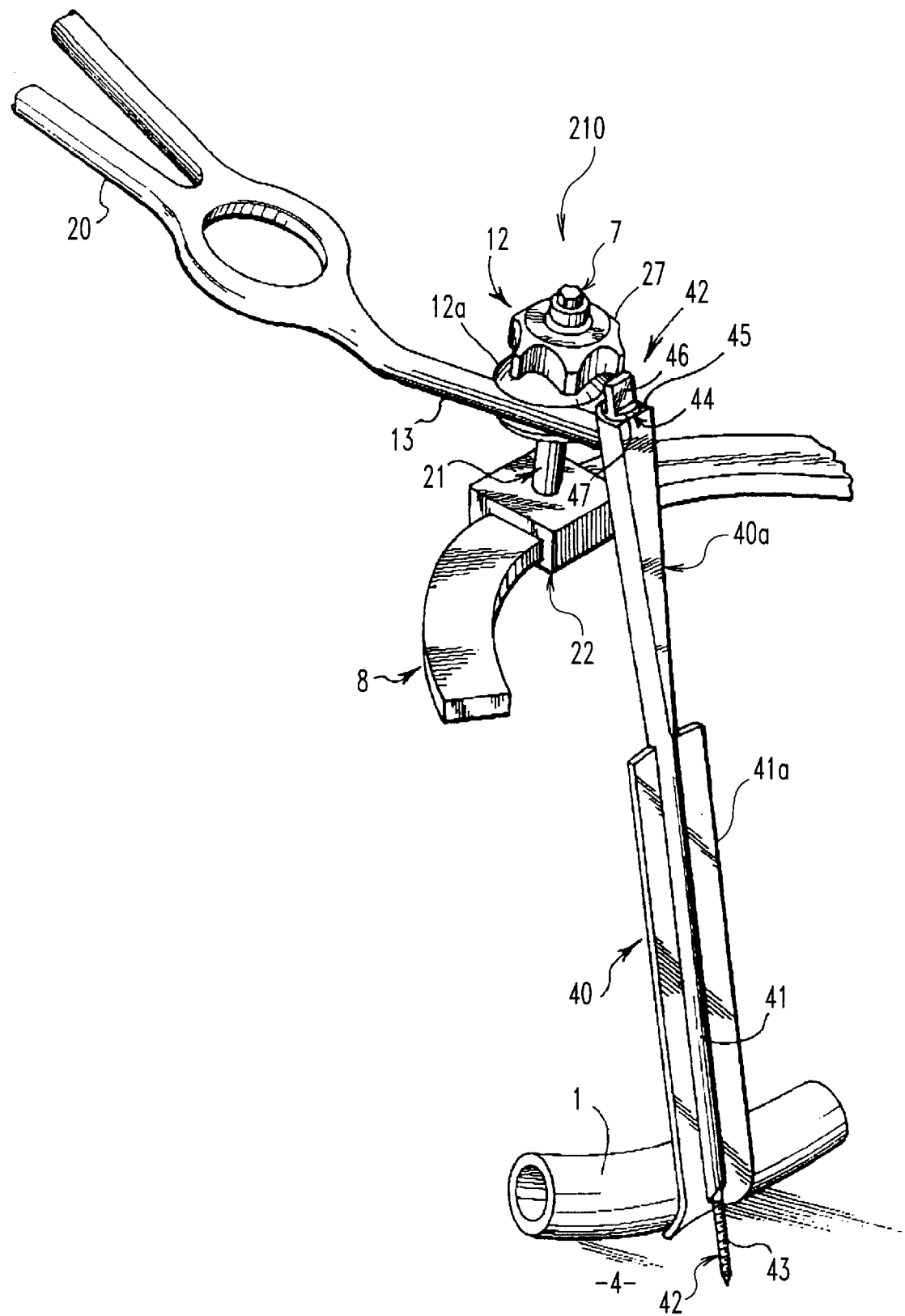
FIG. 6 is a partial perspective view of another embodiment of the instrumentation.

In another embodiment of the invention illustrated in FIG. 6, spinal instrumentation 210 is shown. Instrumentation 210 includes frame 8 and at least one articulated device 7 for connecting a corresponding number of retractors 40a. Retractors 40a include valves 40 coupled to rod 13 with optional handle 20. In FIG. 6, reference numerals like those of FIGS. 1–5 denote like features.

The means for fixing each valve 40 to the bone 4 of the spine comprise, in each valve 40, an axial longitudinal passageway 41 in which is slidable a fixation pin 42 having a screw-threaded end portion 43. Passageway 41 retains pin 42. End portion 43 may be screwed into bone 4 of the spine. Each valve 40 includes a lower plate portion 41a to bear against tissue. The opposite end portion 44 of each pin 42 is shaped for receiving a screwing tool (not shown) and for bearing against the end face 45 of the valve 40 at the end of the screwing.

As illustrated in FIG. 6, the end portion 44 is formed by a head 46 which can cooperate with the aforementioned tool and by a shoulder 47 extending the head 46. At the end of the screwing, this shoulder 47 comes to bear against the transverse end face 45 of the valve 40. Thus the end portion 44 of the pin 42 exerts on the valve 20 a force for maintaining it in position on the bone 4 of the spine. This maintaining force generally reduces risk of an offsetting of the valve 40 with respect to the spine and consequently an untimely repositioning of a vessel 1 in the operating area.

Figure 7:
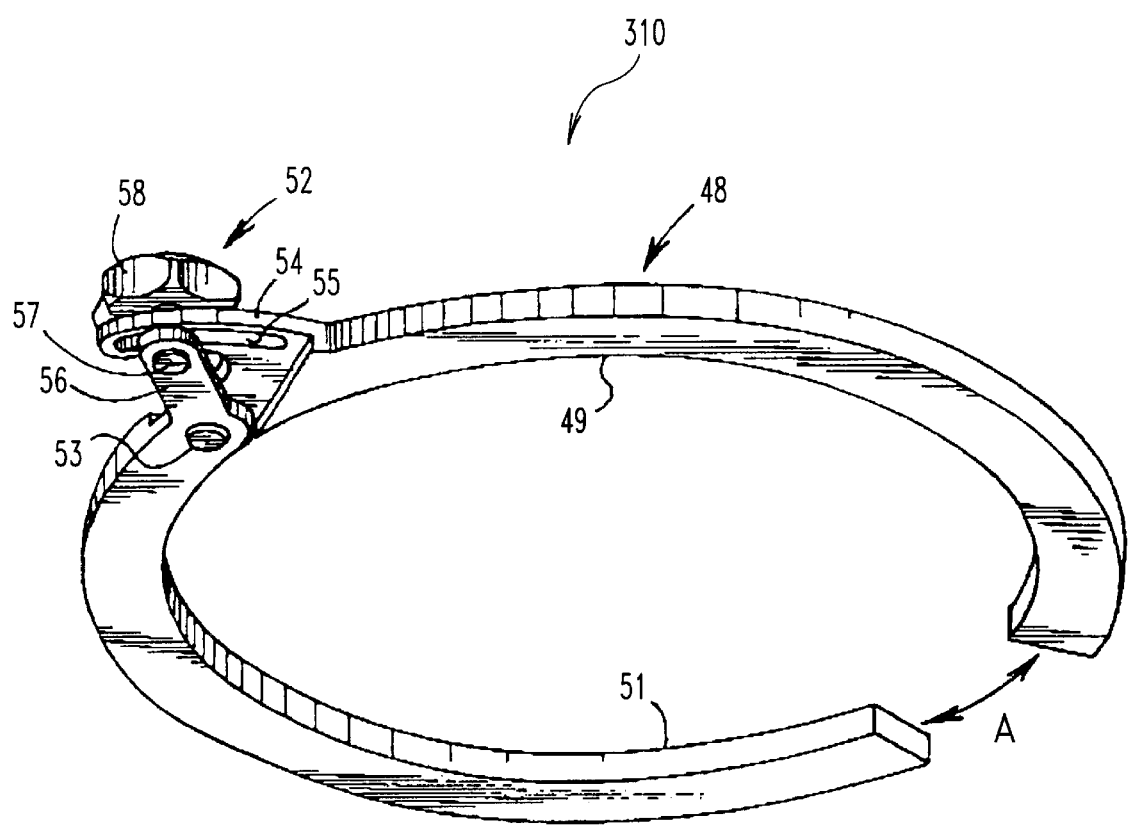
FIG. 7 is a perspective view of a frame of surgical instrumentation of yet another embodiment of the present invention.

In still another embodiment of the invention illustrated in FIG. 7, spinal instrumentation 310 is shown; where reference numerals like those of instrumentation 110, 210 denote like features. Instrumentation 310 includes frame 48. Frame 48 comprises two parts 49, 51 articulated together and capable of being rendered rigid with each other after an adjustment of their angular opening A by a locking device 52. This may be achieved, for example as shown in FIG. 7, in the following manner: the two parts 49, 51 formed by circular sectors are articulated together by a transverse pin 53. One of the two parts, for example the part 49, is extended with respect to the articulation pin 53, by a curved lateral sector 54 in which a circular oblong opening 55 is provided, while the end of the second part 51 is extended by a lug 56 which extends transversely of the sector 54. A screw-threaded pin 57 extends through the lug 56 and the curved opening 55 and is axially engaged by a nut 58 that can be screwed thereon and fixed to the lug 56.

Thus the angular opening A can be adjusted within the limits corresponding to the angular extent of the curved oblong opening 55 in which the screw-threaded pin 57 slides. After the adjustment of the angular spreading apart A by a pivoting about the pin 53, the surgeon can lock the two parts 49, 51 together by tightening the nut 58 on the screw-threaded pin 57. The deformability and adjustability of the frame 48 permits adapting it to the operating area to be created. Instrumentation 48 may be utilized with devices 7 and valves 2, 40 as previously described. The valves 2, 40 are preferably made of a material which permits effecting a radiographic monitoring during the operation, i.e. a material which is radio-transparent or radio-translucid. It is also preferred that this material be selected, for example, from the following group: aluminum, titanium, carbon composites, and plastics.

The scope of the invention is not intended to be limited to the embodiments described hereinbefore and may comprise many variants. Further, the disclosed components, portions, members, parts, devices, operations, processes, and methods may be interchanged, combined, substituted, deleted, rearranged, added, separated into two or more elements, or otherwise modified as would occur to those skilled in the art without departing from the spirit of the present invention. For example, the articulation device 52 may be replaced by any equivalent system as would occur to those skilled in the art. Further, the instrumentation 110, 210, 310 may advantageously comprise a support arm of the frame 8 through the medium of the handle 11, this arm being moreover adapted to be fixed to a surgical table in the known manner. In still other embodiments of the invention, the articulated devices 7 may be replaced by any equivalent system enabling the valves 2 or 40 to be oriented in all directions and adjusted in translation. The support frame 8 may be shaped differently than a ring.

While mount 12a and bearing member 19a are preferably each a one piece structure, in other embodiments, two or more separable pieces may be utilized to provide mount 12a, bearing member 19a, or both. Alternatively or additionally, mount 12a may be arranged for pivotal engagement by a rounded shoulder or ball-shaped bearing member from above instead of riding on top of such a structure.

The device 7, as depicted, provides at least two degrees of rotational freedom and one degree of translational freedom, within corresponding ranges, to adjust orientation of retractor 2b, 40a. However, in other embodiments, one or more of these degrees of freedom may not be needed. For example, mount 12a may be integral with or fixedly connected to retractors 2b, 40a; valves 2, 40; rod 13, or handle 20. Alternatively or additionally, the angular articulation of one or more of devices 7 may be constrained to only one degree of rotational freedom over a given range. This constrained angular range may be accomplished by providing a bearing member in place of a ball-shaped part that is formed with a rounded shoulder which only allows pivoting about one pivot axis. For example, a member having opposing cylindrically shaped shoulders bounded by opposing flat sides may be utilized in a correspondingly shaped receiving socket of a mount.

All publications, patents, and patent applications cited in this specification are herein incorporated by reference as if each individual publication, patent, or patent application were specifically and individually indicated to be incorporated by reference and set forth in its entirety herein. Furthermore, French Patent Application No. 97 13309, filed on 23 Oct. 1997, to which priority is claimed, is hereby incorporated by reference in its entirety. While the invention has been illustrated and described in detail in the drawings and foregoing description, the same is to be considered as illustrative and not restrictive in character, it being understood that only the preferred embodiments have been shown and described and that all changes, modifications and equivalents that come within the spirit of the invention as defined by the following claims are desired to be protected.

What is claimed is:

1. Surgical instrumentation to perform a surgical intervention on a patient's spine, comprising:

a frame;

a number of valves; and a number of articulated devices each corresponding to one of said valves and each being adapted to be rigidly fixed to said frame in a spaced apart relationship from one to another, said devices each including a first portion coupled to a respective one of said valves and a second portion contacting said first portion in a bearing relationship, said second portion defining a passage bounded by a conical bearing surface, said devices each being selectively operable to permit said first portion to slidably pivot about said second portion with two degrees of freedom to adjust angular position of said respective one of said valves over a range of angles generally corresponding to a cone defined by said passage; and wherein said devices are each operable to selectively clamp said respective one of said valves, said first portion, and said second portion together, with said respective one of said valves being in an angular position selected from said range to retract tissue in contact therewith to establish an operating area along the patient's spine.

2. The instrumentation of claim 1, wherein said valves each include a passageway and a fixation pin slidable through said passageway to engage bone.

3. The instrumentation of claim 2, wherein said pin includes a threaded end portion.

4. The instrumentation of claim 1, wherein said second portion of each of said devices includes a hollow, ball-shaped part integrally connected to a sleeve and a device pin slidably passing through said ball-shaped part and said sleeve.

5. The instrumentation of claim 4, wherein said respective one of said valves is integrally and fixedly connected to said first portion.

6. The instrumentation of claim 4, wherein said second portion defines:

a cavity slidably receiving a shifting rod fixed to said respective one of said valves to couple said respective one of said valves to said first portion, said rod having a selectively adjustable translational position in said cavity; and said device pin passing through said passage.

7. The instrumentation of claim 6, wherein said sleeve extends from said ball-shaped part about said pin and is threaded to receive a nut for clamping said respective one of said valves, said first portion, and said second portion together.

8. The instrumentation of claim 6, wherein said ball-shaped part has a number of longitudinal slots.

9. Surgical instrumentation, comprising:

a first retractor;

a second retractor;

a frame interconnecting a first device and a second device in a spaced apart relationship;

said first device operable to connect to said first retractor, said first device including a first ball joint riding on a first device pin coupled to said frame, said first ball joint to angularly position said first retractor over a first range of angles when said first retractor is coupled to said first device, said first device being arranged to selectively fix said first retractor at a first angle selected from said first range; and said second device operable to connect to said second retractor, said second device including a second ball joint riding on a second device pin coupled to said frame, said second ball joint to angularly position said second retractor over a second range of angles when said second retractor is coupled to said second device, said second device being arranged to selectively fix said second retractor at a second angle selected from said second range.

10. The instrumentation of claim 9, wherein said frame is comprised of two parts articulated together and a locking device to selectively fix said two parts to each other with a desired angular opening.

11. The instrumentation of claim 9, wherein said first ball joint includes a bearing member with a hollow, ball-shaped part and a clamp defining a passage shaped to define a socket, said socket receiving said ball-shaped part in a bearing relationship with said clamp riding on said ball-shaped part.

12. The instrumentation of claim 11, wherein said bearing member further includes a sleeve integrally connected to said ball-shaped part, said sleeve extending through said passage and limiting motion of said clamp when said clamp is riding on said ball-shaped part to define said first range of angles as generally corresponding to a cone.

13. The instrumentation of claim 12, wherein said first device pin extends through said bearing member and said passage.

14. The instrumentation of claim 13, wherein said sleeve includes a thread and further comprising a nut, said clamp defines a cavity to receive said first retractor, said nut bearing against said clamp to rigidly fix said first retractor, said clamp and said bearing member together when said nut engages said thread and is tightened, and said first retractor is received in said cavity.

15. The instrumentation of claim 9, wherein:

said first retractor includes a first valve plate fixed to a first shifting rod, said first device includes a first clamp defining a first cavity and a first bearing member, said first rod is slidable within said first cavity to adjust translational position of said first rod relative to said first device, said first bearing member includes a first hollow, ball-shaped part integrally connected to a first threaded sleeve, said first clamp defines a first passage bounded by a first tapered bearing surface in contact with said first bearing member to provide said first ball joint, said first threaded sleeve extends out of said first passage, said first device further includes said first pin passing through said first bearing member and said first passage and a first nut to threadably engage said first threaded sleeve; and said second retractor includes a second valve plate fixed to a second shifting rod, said second device includes a second clamp defining a second cavity and a second bearing member, said second rod is slidable within said second cavity to adjust translational position of said second rod relative to said second device, said second bearing member includes a second hollow, ball-shaped part integrally connected to a second threaded sleeve, said second clamp defines a second passage bounded by a second tapered bearing surface in contact with said second bearing member to provide said second ball joint, said second threaded sleeve extends out of said second passage, said second device further includes said second pin passing through said second bearing member and said second passage and a second nut to threadably engage said second threaded sleeve.

16. Surgical instrumentation, comprising:

a first retractor;

a first articulated device including a first retractor mount to mount said first retractor to said first device, said first device further including a first pin, said first mount defining a first passage through which said first pin passes, said first passage being shaped to selectively move said first mount relative to said first pin with two degrees of freedom over a first range of different angular positions and correspondingly position said first pin over a range of different locations within said passage, said first retractor being angularly adjustable with said first mount when mounted to said first device; and wherein said first device is operable to selectively clamp said first mount and said first pin together to rigidly fix said first retractor at a desired angle selected from said first range when said first retractor is mounted to said first device.

17. The instrumentation of claim 16, wherein said retractor includes a rod and said first mount defines a cavity, said rod is slidable within said cavity to provide a range of translational positions of said rod relative to said first device, and said first device is further operable to clamp said rod, said first mount, and said first pin together to fix said rod at a desired translational position selected from said range of translational positions when said rod is positioned in said cavity.

18. The instrumentation of claim 16, further comprising:

a second retractor;

a second articulated device including a second retractor mount to mount said second retractor to said second device, said second device further including a second pin, said second mount defining a second passage through which said second pin passes, said second passage being shaped to selectively move said second mount relative to said second pin with two degrees of freedom over a second range of different angular positions and correspondingly position said second pin over a range of different locations within said passage, said second retractor being angularly adjustable with said second mount when mounted to said second device; and a frame adapted to interconnect said first device and said second device in a spaced apart relationship; and wherein said second device is operable to clamp said second mount and said second pin together to rigidly fix said second retractor at another desired angle selected from said second range when said second retractor is mounted to said second device.

19. The instrumentation of claim 16, wherein said first device further includes a hollow, ball-shaped part integrally connected to a sleeve, and said first pin passes through said ball-shaped part and said sleeve.

20. The instrumentation of claim 19, wherein said first mount defines a conical bearing surface to engage said ball-shaped part received in a portion of said passage, said sleeve is threaded, and further comprising a nut to engage said sleeve to clamp said first mount and said first pin together when said nut is tightened on said sleeve.

21. The instrumentation of claim 16, further including a fixation pin configured to slide through a retaining passageway defined by said first retractor.

22. Surgical instrumentation, comprising:

a first retractor including a first rod portion;

a first articulated device including a first mount coupled to said first rod portion of said first retractor and a first bearing member, said first bearing member including a first rounded shoulder and a first stem projecting from said first shoulder, said first mount defining a first passage receiving said first shoulder to contact said first mount, said first passage being shaped to permit movement of said first mount along said first shoulder while in contact therewith to angularly adjust said first retractor, said first stem extending through said first passage to limit angular adjustment of said first retractor to a first range of angles; and wherein said first device is operable to selectively clamp said first mount and said first bearing member together to fix said first retractor at a first angle selected from said first range of angles.

23. The instrumentation of claim 22, wherein said first rod portion of said first retractor is slidably coupled within a cavity defined by said first mount to provide a range of translational positions of said rod portion relative to said first device, and said first device is further operable to fix said first rod portion in a desired translational position selected from said range of translational positions when said first mount and said first bearing member are clamped together.

24. The instrumentation of claim 22, further comprising:

a second retractor including a second rod portion;

a second articulated device including a second mount coupled to said second rod portion of said second retractor and a second bearing member, said second bearing member including a second rounded shoulder and a second stem projecting from said second shoulder, said second mount defining a second passage receiving said second shoulder to contact said second mount, said second passage being shaped to permit movement of said second mount along said second shoulder while in contact therewith to angularly adjust said second retractor, said second stem extending through said second passage to limit angular adjustment of said second retractor to a second range of angles;

a frame adapted to interconnect said first device and said second device in a spaced apart relationship; and wherein said second device is operable to selectively clamp said second mount and said second bearing member together to fix said second retractor at a second angle selected from said second range of angles.

25. The instrumentation of claim 22, wherein said first shoulder is provided by a hollow ball-shaped part integrally connected to a sleeve, said sleeve defining at least a portion of said first stem.

26. The instrumentation of claim 25, wherein said first device includes a pin passing through said ball-shaped part and said sleeve to further define said first stem.

27. The instrumentation of claim 22, wherein said first range of angles generally corresponds to a cone about said first stem.

28. The instrumentation of claim 22, further including a fixation pin configured to slide through a passageway defined by said first retractor.

29. A method of performing surgery on a patient's spine, comprising:

mounting a first valve on a frame with a first articulated device, the first valve being fixed to a rod, the first device including a mount defining a cavity for receiving the rod and a bearing member engaged with the mount;

sliding the rod in the cavity to provide a desired translational position of the rod relative the first device;

pivoting the mount about the bearing member to select a desired angular position of the first valve from a range of angles generally corresponding to a cone;

clamping the first valve in the desired translational and angular position; and connecting a second valve on the frame with a second articulated device, the second valve being spaced apart from the first valve, the first valve and the second valve being oriented to shift aside tissue to maintain an operating field along the patient's spine.

30. The method of claim 29, further comprising fixing the first valve to the patient's spine by sliding a fixation pin through a passageway defined by the first valve.

31. The method of claim 30, wherein said fixing includes screwing a threaded end portion of the fixation pin into bone.

32. The method of claim 29, wherein the mount defines a passage receiving at least a portion of the bearing member and the bearing member includes a ball-shaped part slidably engaging a generally conical bearing surface defined within the passage by the mount.

33. The method of claim 29, further comprising:

hooking a nose of a push member on the first valve; and adjusting position of the first valve with the push member.

34. Surgical instrumentation to perform a surgical intervention on a patient's spine, comprising:

a frame;

a number of valves; and a number of articulated devices each corresponding to one of said valves and each being adapted to be rigidly fixed to said frame in a spaced apart relationship from one to another, said devices each including a first portion coupled to a respective one of said valves and a second portion contacting said first portion in a bearing relationship, wherein said second portion of each of said devices includes a hollow, ball-shaped part integrally connected to a sleeve and a device pin slidably passing through said ball-shaped part and said sleeve, said devices each being selectively operable to permit said first portion to slidably pivot about said second portion with two degrees of freedom to adjust angular position of said respective one of said valves over a range of angles; and wherein said devices are each operable to selectively clamp said respective one of said valves, said first portion, and said second portion together, with said respective one of said valves being in an angular position selected from said range to retract tissue in contact therewith to establish an operating area along the patient's spine.

35. The instrumentation of claim 34, wherein said respective one of said valves is integrally and fixedly connected to said first portion.

36. The instrumentation of claim 34, wherein said second portion defines:

a cavity slidably receiving a shifting rod fixed to said respective one of said valves to couple said respective one of said valves to said first portion, said rod having a selectively adjustable translational position in said cavity; and a passage, said device pin passing through said passage.

37. The instrumentation of claim 36, wherein said sleeve extends from said passage about said pin and is threaded to receive a nut for clamping said respective one of said valves, said first portion, and said second portion together.

38. The instrumentation of claim 36, wherein said passage is bounded by a conical bearing surface and said range generally corresponds to a cone.

39. The instrumentation of claim 36, Wherein said ball-shaped part has a number of longitudinal slots.

* * * * *